United States Patent [19]

Taylor et al.

[11] 4,161,616
[45] Jul. 17, 1979

[54] ACROLEIN CONVERSION TO BUTANEDIOL

[75] Inventors: Paul D. Taylor, Corpus Christi, Tex.; Thomas H. Vanderspurt, Gillette; Anthony B. Conciatori, Chatham, both of N.J.

[73] Assignee: Celanese Corporation, New York, N.Y.

[21] Appl. No.: 899,052

[22] Filed: Apr. 24, 1978

[51] Int. Cl.$^2$ .............................................. C07C 31/18
[52] U.S. Cl. ............................. 568/862; 260/346.11; 260/602; 568/598; 568/881
[58] Field of Search ................... 568/862, 598, 881; 260/602

[56] References Cited

U.S. PATENT DOCUMENTS

| 3,686,333 | 8/1972 | Duyverman | 568/881 |
|---|---|---|---|
| 3,929,915 | 12/1975 | Cumbo et al. | 568/862 |
| 3,963,755 | 6/1976 | Cumbo et al. | 568/862 |
| 4,017,550 | 4/1977 | Kummer | 568/863 |
| 4,044,059 | 8/1977 | Copelin | 568/862 |
| 4,079,064 | 3/1978 | Taylor | 568/862 |
| 4,083,882 | 4/1978 | Taylor et al. | 568/862 |

FOREIGN PATENT DOCUMENTS 44-5368 3/1969 Japan ........................................ 568/598

Primary Examiner—Joseph E. Evans
Attorney, Agent, or Firm—Kenneth A. Genoni

[57] ABSTRACT

This invention provides a process for producing 1,4-butanediol by (1) selectively hydrogenating acrolein to a product mixture of allyl alcohol and residual acrolein in a 2:1 ratio, (2) converting the product mixture to acrolein diallyl acetal under acidic conditions, (3) selectively hydroformylating the acrolein diallyl acetal to a trialdehyde, and (4) reacting the trialdehyde under substantially neutral hydrolysis/hydrogenation conditions to yield 1,4-butanediol.

Acrolein is converted into tetrahydrofuran employing the process conditions described above, except that the step (4) hydrolysis/hydrogenation reaction is conducted under acidic conditions.

14 Claims, No Drawings

ACROLEIN CONVERSION TO BUTANEDIOL

BACKGROUND OF THE INVENTION 1,4-Butanediol can be derived from succinic acid, maleic anhydride and other four-carbon organic species, but such methods are not economically attractive. Another method of producing 1,4-butanediol is by the reaction of formaldehyde and acetylene to form 1,4-butynediol as an intermediate, which is subsequently hydrogenated to the desired 1,4-butanediol product.

Other investigators have endeavored to convert acrolein into 1,4-butanediol by subjecting acrolein to hydroformylation conditions, the objective being the formation of succinaldehyde as an intermediate product. The results have been unsatisfactory since the main conversion product recovered from acrolein under hydroformylation conditions is propionaldehyde.

Other efforts to produce 1,4-butanediol have involved hydroformylation of allyl alcohol to yield 4-hydroxybutanal as an intermediate which is subsequently hydrogenated to 1,4-butanediol. The liquid phase hydroformylation of allyl alcohol in the presence of hydroformylation catalysts such as cobalt carbonyl produces significant quantities of propanal, propanol and 2-methyl-3-hydroxypropanal as by-products, in addition to the desired 4-hydroxybutanal.

In U.S. Patent Office Defensive Publication No. 904,021 (Nov. 21, 1972) there is disclosed an improved hydroformylation process for converting unsaturated alcohols into diols. In one embodiment the Publication process involves the hydroformylation of allyl alcohol with rhodium-phosphine complex catalyst to produce a reaction mixture which is subsequently hydrogenated to yield 63 percent 1,4-butanediol and 25 percent 2-methylpropanediol, based on the weight of allyl alcohol charged.

U.S. Pat. No. 4,017,550 describes a method for the manufacture of 1,4-butanediol by hydroformylation of cyclic acetals of acrolein to a 3-formylpropionaldehyde acetal intermediate, and then hydrogenation of the acetal intermediate. U.S. Pat. No. 4,024,197 describes a similar procedure for production of 1,4-butanediol.

U.S. Pat. No. 4,039,592 describes a method of butanediol production which involves (1) reacting propylene and a mixture of methyl acetate, water, acetic acid and methanol with oxygen in the vapor phase in the presence of a Group VIII noble metal catalyst to form allyl acetate, (2) converting the allyl acetate under hydroformylation conditions to a mixture containing monoacetate ester of 1,4-butanediol and 1,2-butanediol, and (3) de-esterifying the mixture under methanolysis conditions to yield the corresponding butanediols.

Tetrahydrofuran is another important organic commodity. It finds application as a versatile solvent medium and as an intermediate for the production of resins and other commercial products such as butyrolactone and succinic acid.

Tetrahydrofuran can be produced by catalytic hydrogenation of maleic anhydride or furan, as is described in patent literature such as U.S. Pat. No. 2,772,293; U.S. Pat. No. 2,846,449; U.S. Pat. No. 3,021,342; and references cited therein.

It is well known that tetrahydrofuran can be produced by a series of reactions starting with the reaction of aqueous formaldehyde and acetylene in the presence of a cuprous acetylide complex to form butynediol. An alkaline material such as the carbonate, bicarbonate or hydroxide of an alkali or alkaline earth metal is commonly added to this reaction to control pH. This alkaline material generally reacts with the formic acid generated in this reaction to form the metal formate. The product of this reaction is then passed to a hydrogenation zone where the butynediol is converted to 1,4-butanediol. The 1,4-butanediol is then converted to tetrahydrofuran employing about 10 percent sulfuric acid. This reaction is conducted under temperature conditions which permit recovery of tetrahydrofuran and water overhead from the reactor. The reaction medium in the reactor typically contains about 50-60 percent unconverted 1,4-butanediol, about 10 percent acid, about 10 percent water, and about 25 percent combined tars and salts. The build-up of tars and salts in the reactor is an undesirable characteristic of this type of process.

There is a need for new and improved commercial processes for the large volume production of both 1,4-butanediol and tetrahydrofuran. The development of such processes in under active investigation.

Accordingly, it is an object of the present invention to provide a new and efficient method for producing 1,4-butanediol.

It is another object of this invention to provide a new and efficient method for producing tetrahydrofuran.

It is a further object of the present invention to provide an economically feasible process for converting acrolein into 1,4-butanediol or tetrahydrofuran on a commercial scale.

Other objects and advantages shall become apparent from the accompanying description and examples.

DESCRIPTION OF THE INVENTION

One or more objects of the present invention are accomplished by the provision of a process for converting acrolein into 1,4-butanediol which comprises (1) selectively hydrogenating acrolein to a product mixture consisting of at least two moles of allyl alcohol per mole of acrolein and propionaldehyde, (2) subjecting the product mixture to acidic conditions to produce acrolein diallyl acetal and propionaldehyde diallyl acetal, (3) selectively hydroformylating the acetals to form a hydroformylation product mixture of

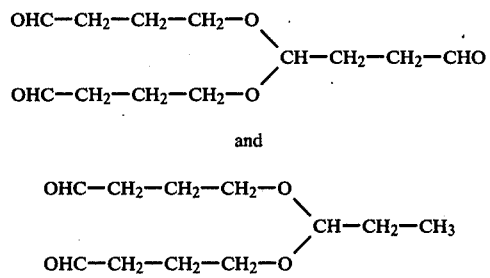

and and (4) subjecting the hydroformylation product mixture to aqueous hydrolysis/hydrogenation conditions to yield 1,4-butanediol.

In a similar process, described more fully hereinbelow, acrolein is converted to tetrahydrofuran. If the step (4) aqueous hydrolysis/hydrogenation reaction is conducted under substantially neutral conditions, then 1,4-butanediol is the major product. If the step (4) aqueous hydrolysis/hydrogenation is conducted under acidic conditions, then tetrahydrofuran is the major product.

Selective Hydrogenation Of Acrolein

The primary objective of the selective hydrogenation step (1) of the invention process is to convert acrolein to allyl alcohol with the substantial exclusion of other hydrogenation byproducts.

Several methods are known in the prior art for converting $\alpha,\beta$-olefinically unsaturated carbonylic compounds into the corresponding $\alpha,\beta$-olefinically unsaturated alcohols, and various selective catalysts are provided for improved conversion and yields.

British Pat. No. 734,247 and U.S. Pat. No. 2,763,696 disclose a process whereby acrolein may be converted to allyl alcohol by means of a vapor phase hydrogenation process. According to this process, moderate yields of allyl alcohol are obtained when acrolein is treated with free hydrogen in the vapor phase at a temperature between 210° C. and 240° C. in the presence of a catalyst comprising cadmium and one or more heavy metals of groups I, II, VI and VIII of the periodic table. Relatively high pressures are employed in the process on the order of 20 to 50 kilograms per square centimeter.

German Pat. No. 858,247 discloses a somewhat different process which is also useful for the conversion of acrolein to allyl alcohol. According to the German patent, good yields of allyl alcohol are obtained by reacting acrolein with free hydrogen in the presence of a catalyst containing cadmium oxide and a metal hydrogenating component which is preferably copper. The patent teaches that the best results are obtained when the process is operated at high temperatures and at high pressures on the order of 100-300 atmospheres.

It is also known to convert $\alpha,\beta$-unsaturated aldehydes into the corresponding unsaturated alcohols in the liquid phase by means of hydrogenation in the presence of a mixture of a copper soap and cadmium soap. It is assumed that the copper salt is the catalyst and that the cadmium salt only serves the function of preventing the copper salt from being reduced to metallic copper. The use of a solution of a mixture of a copper salt and a cadmium salt for catalyst has the disadvantage that the system is extremely unstable under the required processing conditions, and fluctuations in conditions can cause reduction of the $Cd^{2+}$ salt and/or the $Cu^{2+}$ salt to metals.

U.S. Pat. No. 3,686,333 describes a liquid phase hydrogenation process for converting alkenals into alkenols in the presence of a catalyst mixture of a cadmium salt of a fatty acid and a transition metal salt of a fatty acid.

Japanese Pat. No. 73-01,361 discloses a process for hydrogenating $\alpha,\beta$-olefinically unsaturated aldehydes into the corresponding allylic alcohol derivatives. The efficiency of the process is improved by the recycle of by-products to the hydrogenation zone, or by passage of the by-products stream into a second hydrogenation zone. The preferred catalysts are mixtures of cadmium and copper, cadmium and silver, cadmium and zinc, cadmium and chromium, copper and chromium, and the like. The Japanese patent discloses that under steady state conditions 1.5 moles/hour of acrolein are converted to 1.05 moles/hour of allyl alcohol and 0.4 mole/hour of n-propanol.

For the purposes of the present invention, it is desirable to convert acrolein into allyl alcohol with an efficiency of at least 95 percent. This objective cannot be readily achieved by the selective hydrogenation catalysts known in the prior art.

It has been found that optimal results in the step(1) selective hydrogenation of acrolein to allyl alcohol can be accomplished by the use of a catalyst composition which consists essentially of a silver-cadmium alloy on a carrier substrate, wherein the atomic ratio of silver to cadmium in the alloy is in the range of between about 0.1 and 3 to 1.

The carrier substrate can be selected from silica, Celite, diatomaceous earth, kieselguhr, alumina, silica-alumina, titanium oxide, pumice, carborundum, boria, and the like. It is highly preferred that the silver-cadmium alloy be supported on a silica and/or alumina carrier substrate. The quantity of carrier substrate in the catalyst composition can vary in the range of between about 5 and 99.5 weight percent, based on the total catalyst weight.

The preferred catalysts are prepared by coprecipitating hydroxides of silver and cadmium from an aqueous solution of calculated quantities of water-soluble salts of silver and cadmium. The precipitation is effected by the addition of caustic to the aqueous solution.

The carrier substrate component of the catalyst composition can be incorporated during the catalyst preparation by slurrying the finely divided carrier substrate mass in the said aqueous medium immediately after the silver-cadmium hydroxides are precipitated. Finely divided porous materials such as fumed silica or diatomaceous earth are highly preferred carrier substrate materials for the preparation of the catalysts.

After the coprecipitation of silver-cadmium hydroxides has been accomplished, the solids phase is recovered by filtration or other conventional means. The filtered solids are washed with chloride-free water until essentially neutral. For the purposes of a fixed bed operation, the dried filter cake preparation is calcined at a temperature between about 175° C. and 300° C. for a period of about two to twenty hours or longer, and then the calcined material is ground and pelleted. Prior to use the catalyst pellets can be reduced in a stream of hydrogen at a temperature between about 50° C. and 250° C. for a period of about five hours. For a fluidized bed operation, the calcined catalyst preparation can be ground and sized in a conventional manner to satisfy process design requirements. The reduction of the catalyst can also be accomplished in situ during the vapor phase hydrogenation process.

There are several critical aspects of catalyst preparation which must be respected in order to achieve a hydrogenation catalyst having unique and advantageous properties in comparison to prior art catalysts for selective hydrogenation of acrolein to allyl alcohol.

Firstly, the silver-cadmium alloy in the catalyst must contain an atomic ratio of silver to cadmium in the range between about 0.1 and 3 to 1, and preferably between about 0.4 and 2.2 to 1.

Secondly, the silver and cadmium in the catalyst must be in the free metal state, and must be substantially in the form of an alloy, i.e., x-ray diffraction spectra should confirm the absence of unalloyed silver or cadmium crystals. Preferred silver-cadmium alloy catalysts are solid solutions which nominally exhibit an x-ray diffraction pattern which is substantially free of detectable unalloyed metal crystallite lines.

In terms of x-ray diffraction data, a preferred silver-cadmium alloy catalyst can consist substantially of $\alpha$-phase silver-cadmium, without detectable splitting of x-ray diffraction lines which is indicative of silver-rich and/or cadmium-rich $\alpha$-phase crystallites. Silver-cadmium catalysts which also have outstanding selectivity for high yield conversion or acrolein into allyl alcohol are those in which the alloy composition consists of more than about 50 percent of γ-phase silver-cadmium crystallites as characterized by x-ray diffraction pattern. Another preferred silver-cadmium alloy catalyst can have α,γ and ε-phase crystallites present. Those especially rich in ε-phase, while very highly selective, are somewhat less active than those richer in nonsplit α-phase alloy.

Thirdly, it has been found that the production of silver-cadmium alloy catalysts, which exhibit the greatest selectivity for converting acrolein to allyl alcohol, can be achieved if the coprecipitation step of the catalyst preparation is conducted within restricted limitations and under controlled conditions. Thus, the total concentration of the water-soluble salts (e.g., nitrate salts) in the aqueous solution should be maintained in the range between about 5 weight percent and the solubility limit of the salts, and the quantity of caustic added as a precipitating agent should approximate the stoichiometric amount within narrow limits. It is particularly advantageous to employ a water-soluble hydroxide (e.g., an alkali metal hydroxide) as the caustic precipitating agent, and to add the caustic rapidly with vigorous stirring to facilitate formation of a precipitate of fine crystals or gel.

Other precautions must be observed during catalyst preparation if highly selective silver-cadmium alloy compositions are to be achieved. It has been found that the calcination step of the catalyst preparation most advantageously must be conducted within narrowly controlled limitations. The calcination step should be accomplished at a temperature between about 175° C. and 300° C., and most preferably at a temperature between 200° C. and 250° C. If calcination of a silver-cadmium alloy catalyst is conducted at a temperature above about 300° C., the resultant catalyst exhibits less selectivity for high efficiency conversion of acrolein to allyl alcohol in step(1) of the invention process.

It has also been found that the silver-cadmium alloy catalysts are most effective when supported on a carrier substrate, i.e., in combination with an internal diluent. Catalysts prepared without a carrier substrate have been found to have lower activity and shorter catalyst life than the corresponding supported catalysts in vapor phase hydrogenation processes. A typical carrier substrate will have an initial surface area of more than about 1–10 m$^2$/gm, and an average pore diameter greater than about 20 Å. A high proportion of small pores is detrimental to catalyst activity, if the size of the pores are such that capillary condensation of an acrolein-type compound occurs and causes pore blockage. This results in loss of catalytic activity.

The desired supported silver-cadmium alloy catalysts can be achieved by introducing a calculated quantity of silver and cadmium complexes or salts in solution into the pores of a support such as silica or controlled pore size glass. The amount of each and the total concentration is adjusted so as to achieve the desired metal ratio and total percent by weight alloy. The solvent is then removed in a manner conducive to the intimate co-deposition of the silver and cadmium complexes or salts on the interior surfaces of the pores. In the case of aqueous silver and cadmium nitrate solutions in silica, exposure of the support and adsorbed solution at room temperature under partial vacuum with about 100 Torr helium present to a vapor trap held at 77° F. for about 48 hours is a convenient procedure. After solvent removal, alternate degassing and reducing conditions are imposed by exposure at elevated temperatures to a vacuum alternated with a low pressure stream of a reducing gas such as hydrogen, synthesis gas, carbon monoxide or hydrazine. The catalyst is then allowed to cool under at least one atmosphere of hydrogen. X-ray diffraction is conveniently employed to verify that alloy formation is complete. Catalysts prepared in this manner are not subjected to conventional air calcination conditions. The catalysts are stored in a relatively oxygen-free environment until usage.

Another highly preferred catalyst for selective hydrogenation of acrolein to allyl alcohol is one consisting essentially of a silver-cadmium-zinc alloy on a carrier substrate, wherein the atomic ratio of silver to cadmium in the alloy is in the range of between 0.1 and 3 to 1, and the zinc is contained in the alloy in a quantity between about 0.001 and 30 weight percent, based on the total weight of alloy. The silver-cadmium-zinc alloy catalyst tends to exhibit improved catalyst life in comparison with a silver-cadmium alloy catalyst.

In the practice of the invention process selective hydrogenation step(1), the acrolein and hydrogen at elevated temperature and pressure are passed in vapor phase through a reaction zone containing a catalyst which has exceptional selective hydrogenation activity, e.g., a silver-cadmium alloy or silver-cadmium-zinc alloy catalyst as described hereinabove.

The reaction temperature of the hydrogenation process can vary in the range between about 0° C. and 300° C., and preferably between about 75° C. and 250° C., and most preferably between about 100° C. and 215° C.

The pressure of the hydrogenation process can vary in the range between about 15 and 15,000 psi, and preferably between about 75 and 5000 psi, and most preferably between about 250 and 2500 psi.

The mole ratio of hydrogen to acrolein in the vapor phase feed stream can vary in the range between about 1:1 and 1000:1. The preferred mole ratio of hydrogen to acrolein in the feed stream is in the range between about 5:1 and 200:1, and most preferred mole ratio in the range between about 10:1 and 150:1.

The rate at which the vapor phase gas stream is contacted with the selective hydrogenation catalyst is not critical, and can be varied consonant with the other processing conditions to achieve an optimal balance of conversion and yield parameters. The flow rate of feed gas reactants can vary over a broad range between about a total of 10 moles and 1000 moles of feed gas reactants per liter of catalyst per hour. A preferred flow-rate of feed gas reactants is one which provides a catalyst contact time between about 0.1 and 50 seconds. By the invention process step(1), acrolein can be converted to allyl alcohol with a space-time yield of greater than 900 grams per liter of catalyst per hour.

The process can be conducted either by passing the feed mixture through a fixed catalyst bed, or through a reactor wherein the catalyst is present in finely divided form and is maintained in a fluidized state by the upward passage therethrough of the gaseous reactants. The process is most conveniently carried out in a continuous manner, although intermittent types of operation can be employed. In a preferred method of continuous operation, the components of the feed stream are brought together and under the desired pressure are passed in vapor phase through the catalyst heated to the desired temperature. The reaction zone advantageously is an elongated tube or tubes containing the catalyst. The feed can be brought into contact with the catalyst in either the unheated or preheated condition. The effluent from the reactor is employed directly in step(2) of the invention process. As a theoretical model, the effluent mixture ideally is composed solely of allyl alcohol and acrolein, in a 2:1 molar ratio. In actual practice, the reaction parameters are adjusted to compensate for the production of propionaldehyde byproduct. The presence of a small quantity of propanol can generally be disregarded.

The desired level of acrolein conversion under reaction conditions providing a known efficiency to allyl alcohol can be calculated by the following equation:

$$2[(1 - C) + (1 - E)C] = EC$$

$$\text{or } C = \frac{2}{3E}$$

wherein $C = \frac{\text{moles acrolein converted}}{\text{moles acrolein feed}}$ $E = \frac{\text{moles of allyl alcohol produced}}{\text{moles of acrolein converted}}$ $1 - C$ = moles of unconverted acrolein $(1 - E)C$ = moles or propionaldehyde produced $EC$ = molar yield of allyl alcohol Hence, for a conversion efficiency of 76 percent, the reaction conditions are adjusted for an 88 percent conversion of the acrolein feed stream.

It is a necessary precaution to insure that free acrolein does not enter into the step(3) hydroformylation zone. It is advantageous to provide that the quantity of allyl alcohol in the feed stream to step(2) of the invention process is at least sufficient to satisfy the stoichiometry of acetal formation with acrolein and propionaldehyde. Thus, 2-2.2 moles of allyl alcohol is required per mole of acrolein and propionaldehyde in the feed stream for step(2) of the invention process. The quantity of propanol present may be included in the allyl alcohol calculation if desired, since it also is involved in acetal formation.

Production Of Acrolein Diallyl Acetal

In a preferred embodiment, the effluent stream is introduced directly into step(2) of the invention process. It is an important aspect of the present invention process that substantially no residual acrolein is to be present in the acrolein diallyl acetal product mixture after the completion of the step(2) procedure. If necessary, the ratio of allyl alcohol and acrolein can be adjusted to insure that the quantity of acrolein reactant present in step(2) of the process is completely exhausted. Under normal circumstances, no adjustment of allyl alcohol/acrolein ratio is required because the effluent stream from step(1) of the process is controlled to contain the proper balance of allyl alcohol, acrolein, propanol and propionaldehyde, which all enter into acetal formation in Step(2).

Step(2) of the invention process can be conducted either batchwise or continuously. Methods of direct condensation of $\alpha,\beta$-unsaturated aldehydes with alcohols are well-known in the chemical literature.

U.S. Pat. No. 3,014,924 describes the reaction of an $\alpha,\beta$-unsaturated aldehyde with an aliphatic polyol in the presence of a catalyst comprising a highly-porous solid carrier having a surface area of at least 75 square meters per gram and about from 0.025 to 1.0 millimole per unit weight of carrier of a strong mineral acid.

U.S. Pat. No. 2,888,492 describes a process for producing acetals which involves reacting an acrolein type aldehyde with a polyol in the presence of 0.02 to 0.06 mole percent based on the amount of ethylenic aldehyde present of a sulfo acid such as sulfuric acid, p-toluene sulfonic acid, ethanesulfonic acid, and the like. The reaction is carried out by heating a mixture of the chosen $\alpha,\beta$-ethylenic aldehyde and polyol dissolved or suspended in a suitable liquid such as, for instance, benzene, dichloroethylene, and the like. By refluxing at about 50° C. to 90° C. under a phase-separating head until the theoretical amount of water is removed, the reaction is completed in about 1 to 3 hours.

For the purposes of the present invention process, step(2) is conducted for a sufficient period of time to permit the condensation reaction between allyl alcohol and acrolein to reach a state of reaction equilibrium at a given temperature. Generally, higher temperatures favor a faster rate of condensation, and concomitantly a lower equilibrium conversion of allyl alcohol/acrolein to acrolein diallyl acetal. Lower temperatures favor a slower rate of condensation but higher conversion to acetal at equilibrium. The removal of water from the reaction medium increases the equilibrium concentration of the acetal species, so that when all of the water is removed only the acetal species remains.

The reaction temperature of the present invention step(2) condensation procedure can vary in the range between about $-20°$ C. and 100° C., and normally is in the range between about $-10°$ C. and 75° C. The preferred condensation reaction temperature is in the range between about 10° C. and 60° C.

The use of solid cation exchange resins as acid catalysts is particularly advantageous in the practice of step(2) of the present invention process. Optimal yield of acrolein diallyl acetal is obtained with ease and efficiency. Cation exchange resins in acid form which are suitable as catalysts are commercially available with well characterized shapes, sizes, surface areas, pore sizes, exchange capacities, moisture content, acid strength, and the like. The technology of solid cation exchange resin acids is reviewed by R. M. Wheaton and A. H. Seamster in the Kirk-Othmer Encyclopedia of Chemical Technology, 2nd Ed., Vol. II, pp. 871–899.

For the purposes of step(2) of the present invention process, strong acid cation exchange resins are highly preferred. These are generally copolymers of polystyrene-divinylbenzene which have benzenesulfonate groups as acid sites. Neutralization of the acid sites transforms the free acid structure into a salt. Commerical cation exchange resins are supplied both in the form of free acids and salts. Illustrative of commercial strong acid cation exchange resins are Rexyn 101 (H+) from Fisher Scientific; Dowex 50 W and Dowex MSC-1 from Dow Chemical; Amberlite 200, 200C and 252 from Rohm and Haas; Ionac C-244, C-249, C-252 and CFP-105(H+) from Ionac Chemical; and the like.

These cation exchange resins have relatively high moisture content (40–60 weight percent) and high cation exchange capacities, i.e., 1–2 meq./gram(wet) and 4–5 meq./gram(dry). It has been found that even with relatively high moisture contents these cation exchange resins are amenable for application in non-aqueous media or in organic solutions containing low concentrations of water, such as are encountered in the practice of the present invention process.

Particularly useful in step(2) of the present invention process are commercial strong acid cation exchange resins adapted for non-aqueous catalyst applications. Illustrative of such cation exchange resins are Amberlyst 15, Amberlyst XN 1005 and Amberlyst SN 1010 which are supplied by Rohm and Haas. These special cation exchange resins have a moisture content less than about 3 percent.

Weakly acidic cation exchange resins are also commercially available. Characteristically these resins have carboxylate functionality rather than sulfonate functionality. Typical commercial products are Amberlite IRC-84, IRC-50, IRC-72 and DP-1 (Rohm and Haas). Employing a weakly acidic cation exchange resin catalyst in the present invention process necessitates a longer reaction time to achieve the optimum allyl alcohol/acrolein condensation reactivity under given process conditions.

An exceptionally high rate of conversion of allyl alcohol/acrolein to acrolein diallyl acetal can be achieved by employing perfluoro sulfonic acid resin as a catalyst. For example, a feed stream of allyl alcohol/acrolein passing through a fixed bed of Nafion 501 powder (DuPont) at ambient temperature and a LHSV of 12 can yield 16 moles of acetal per liter per hour.

The acid catalyst activity tends to decline after long term use in a fixed bed, or in a slurry bed reaction medium where the feed is introduced continuously and the product mixture is withdrawn continuously. Spent acid cation exchange resins are readily reactivated by treatment with an acid solution.

In a batch-type procedure employing a solid catalyst, an acid cation exchange resin is employed in a quantity at least sufficient to catalyze the allyl alcohol/acrolein condensation reaction to produce a high yield of acrolein diallyl acetal. The quantity of acid cation exchange resin employed as a catalyst can vary over a broad range between about 0.1 and 20 weight percent, based on the weight of acrolein in the reaction mixture.

In a preferred embodiment of the step(2) procedure, the acid cation exchange resin is charged to a fixed bed reactor, and at ambient temperature and pressure a feed stream of allyl alcohol and acrolein is passed through the fixed bed of resin catalyst. The liquid hourly space velocity of the feed stream can vary over a range between about 0.1 and 50. The LHSV is preferably about 1-20, and most preferably about 10-15.

There are several advantages relating to the use of a strong acid cation exchange resin as a catalyst in step(2). In both slurry bed and fixed bed reaction systems, the heterogeneous catalyst phase remains separate from the resultant product phase. No neutralization of acid catalyst is required, and the heterogeneous catalyst phase is undiminished and reusable.

A further advantage of step(2) of the present invention process derives from the fact that the resultant product mixture consisting essentially of acrolein diallyl acetal and water can be subjected to step(3) hydroformylation conditions directly. The presence of water in the feed mixture is not deleterious.

Hydroformylation Of Acrolein Diallyl Acetal

Step(3) of the present invention process is accomplished by reacting the effluent stream (i.e., acrolein diallyl acetal) from step(2) with hydrogen and carbon monoxide under hydroformylation conditions in the presence of a hydroformylation catalyst.

The preparation of aldehydes and alcohols by the reaction of an olefin with hydrogen and carbon monoxide in the presence of a catalyst is well known in the art, i.e., the "oxo" or "Roelen" reaction. The reaction of an olefin with carbon monoxide and water employing cobalt carbonyl, nickel carbonyl or iron carbonyl is known to produce carboxylic acids (see U.S. Pat. No. 2,448,368 and U.S. Pat. No. 2,593,440). The reaction of an olefin with carbon monoxide and water produces alcohols when conducted in the presence of an iron carbonyl-tertiary amine complex catalyst [Reppe synthesis; Liebig's Ann. Chem., 582, 133(1953)].

Cobalt catalysts for hydroformylation of olefins to produce alcohols and aldehydes are described in Kirk-Othmer, Encyclopedia of Chemical Technology, 14, 372, 2nd Ed. Cobalt catalysts are also reviewed in "Catalysis Reviews", 6, 85–131 (1972), published by M. Dekker Inc.

Catalysts which are suitable for the invention step(3) hydroformylation procedure are illustrated by those described in U.S. Pat. Nos. 3,168,553; 3,239,556; 3,239,570; 3,290,379; 3,369,050; 3,420,898; 3,488,296; 3,527,818; 3,725,534; 3,816,337; 3,821,311; 3,825,601; 3,847,997; 3,857,900; 3,859,369; and the like.

Further, any of the metal-phosphine complexes disclosed in "Carbon Monoxide in Organic Synthesis", Falbe, (Springer-Verlag 1970), pp. 14–25, may be used. The preferred catalysts are phosphine complexes of rhodium, cobalt, iridium and ruthenium. The most preferred catalysts have the formula $RhCOH(Q_3P)_3$, $RhCOH[(QO)_3P]_3$, $RhCOCl[(QO)_3P]_2$ and $RhCOCl(Q_3P)_2$ wherein Q is phenyl; alkyl phenyl such as tolyl, xylyl, and the like; cyclohexyl; alkyl substituted cyclohexyl such as methyl, propyl, octyl, and the like; substituted cyclohexyl; and aliphatic radical such as methyl, butyl, octyl, and the like, or mixtures of any of the foregoing. Rhodium catalysts containing tertiary amines are also important hydroformylation catalysts, e.g., a catalyst complex of rhodium metal, carbon monoxide and a trialkyl amine, triaryl amine or trialkylaryl amine.

Superior results are achieved if the step(3) hydroformylation reaction is conducted in the presence of a catalyst which is a complex of a Group VIII metal and a ligand containing phosphorus, arsenic and/or antimony elements. Tertiary amines can also be employed as a ligand in the catalyst complex.

It is worthy of note that an exceptionally high yield of straight chain trialdehyde product can be obtained in step(3) when the hydroformylation catalyst employed is a complex of rhodium metal, carbon monoxide and triaryl phosphine. Illustrative of this class of catalysts is

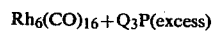

$Rh_6(CO)_{16} + Q_3P(excess)$

It is also to be noted that straight chain selectivity of product yield is promoted when the molar ratio of triaryl phosphine ligand to rhodium metal in the hydroformylation reaction medium is at least 10 to 1, and as high as 400 to 1. Hence, a higher yield of straight chain trialdehyde is obtained at the expense of branched chain trialdehyde:

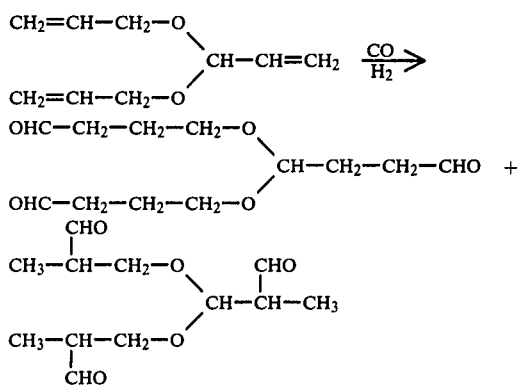

It is to be noted that in the present invention process propionaldehyde diallyl acetal is formed as a minor byproduct in step (2), and is hydroformylated to a dialdehyde in step (3) of the invention process:

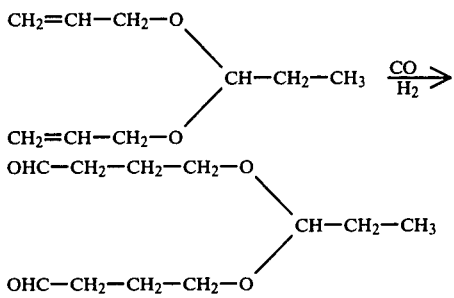

One method for producing the desired straight chain trialdehyde in high yield selectivity of at least 70 weight percent comprises reacting acrolein diallyl acetal with hydrogen and carbon monoxide in the presence of a preferred hydroformylation catalyst as described hereinabove at a temperature between about 25° C. and 200° C. and a pressure between about 15 and 3000 psi.

Illustrative of a preferred embodiment, straight chain trialdehyde product can be produced in a yield of at least 80 weight percent by reacting acrolein diallyl acetal with hydrogen and carbon monoxide in the presence of a metal-ligand complex hydroformylation catalyst at a temperature between 80° C. and 120° C. and a pressure between about 75 and 150 psi. The relative amounts of hydrogen and carbon monoxide employed can vary in accordance with conventional hydroformylation processes, i.e., a molar ratio between 10:1 and 1:10. A high yield of straight chain trialdehyde is favored by increasing the relative ratio of hydrogen to carbon monoxide. Hence, to achieve the conversion of acrolein diallyl acetal to straight chain trialdehyde in a yield of 85 weight percent and higher, a molar ratio of 1:1 to 5:1 of hydrogen to carbon monoxide is employed in the presence of a hydroformylation catalyst which is a complex of a Group VIII metal and a ligand containing phosphorus, arsenic and/or antimony elements.

The hydroformylation catalyst is generally employed in a quantity between about 0.001 and 5 weight percent, based on the weight of acrolein diallyl acetal starting material, and preferably a weight percent quantity between about 0.01 and 1.0, exclusive of the weight of ligand if present.

The step (3) hydroformylation reaction of the invention process may be carried out in a solvent, preferably one which is inert with respect to the products or starting materials, if desired. The solvent generally dissolves the catalyst, starting material and products. A wide variety of organic solvents such as, for example, aromatics, aliphatics, esters, ethers, nitriles, alcohols, halogenated hydrocarbons, and the like, including benzene, cyclohexane, ethyl acetate, methyl alcohol, ethyl orthoformate, tetrahydrofuran, dioxane, isopropyl alcohol, aliphatic hydrocarbon cuts (saturated), chlorobenzene, methylene chloride, propionitrile, acetonitrile, trimethyl acetonitrile, and the like, and mixtures thereof may be employed.

For the operation of the step (3) hydroformylation procedure on a large scale, it is advantageous to exclude any solvent from the reaction medium. Excellent results can be achieved, for example, by employing a rhodium carbonyl catalyst component which is incorporated in a large excess of triphenyl phosphine. The said triphenyl phosphine can be included in the reaction medium in a quantity which is between 20 and 90 percent of the total weight of catalyst and acrolein diallyl acetal reactant. Triphenyl phosphine at a temperature above about 80° C. is highly fluid and performs as an excellent medium for the step (3) hydroformylation procedure.

If desired, the step (3) hydroformylation procedure can be conducted under conditions which are selected to yield a trihydric polyol derivative rather than a trialdehyde derivative as the product. Hence, the present invention contemplates a step (3) procedure which comprises (1) reacting acrolein diallyl acetal with hydrogen and carbon monoxide in the presence of a metal-ligand complex hydroformylation catalyst at a temperature between about 80° C. and 120° C. and a pressure between about 300 and 3000 psi to form the trialdehyde, and (2) increasing the temperature to above about 150° C. to convert said trialdehyde to trihydric polyol.

Preferred catalysts for the two-phase procedure for producing the trihydric polyol derivative are cobalt metal hydroformylation catalysts which are phosphine-modified. A suitable catalyst for such a process is a complex of cobalt metal, carbon monoxide and trialkyl phosphine (e.g., tributyl phosphine).

The temperature in the second phase of the hydroformylation procedure is maintained in the range between about 150° C. and 225° C., and preferably at about 190° C. The pressure in the hydroformylation system is maintained in the range between about 300 and 3000 psi, and preferably between about 500 and 1000 psi.

The products of the step (3) hydroformylation procedure may be recovered by distillation or other conventional methods. In Example IX illustrated hereinbelow, straight chain trialdehyde product from step (3) is recovered by precipitating the trialdehyde from a concentrated filtrate by diluting the filtrate with a non-solvent for the said product.

Hydrolysis/Hydrogenation Of Trialdehyde

In step (4) of the invention process, trialdehyde (and/or trihydric polyol) product from the step (3) hydroformylation zone is subjected to hydrolysis/hydrogenation under substantially neutral conditions to yield 1,4-butanediol:

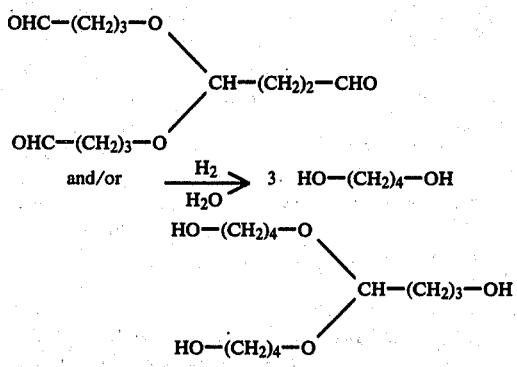

In accordance with one embodiment of step (4) of the present invention process, straight chain trialdehyde and/or trihydric polyol as illustrated above is contacted with hydrogen in the presence of a hydrogenation catalyst and water in a reaction medium maintained at a pH in the range between about 4 and 8, and at a temperature between about 150° C. and 250° C. and a pressure between about 15 and 1500 psi.

The hydrogenation catalysts suitable for use include metal catalysts such as platinum, palladium, silver, copper, vanadium, tungsten, cobalt, nickel, iron, ruthenium, rhodium, manganese, chromium, molybdenum, iridium, titanium, zirconium, and the like, and mixtures of the same and compounds and alloys thereof as described in prior art such as U.S. Pat. No. 2,840,617.

The hydrogenation catalyst can be employed in a finely divided form as a dispersion throughout the reaction medium. Or, the catalyst may be employed in the form of beads or pellets and the like, either in a pure state or supported upon or carried by an inert or catalytically active supporting or carrier material such as pumice, kieselguhr, diatomaceous earth, clay, alumina, charcoal, carbon, or the like. In the latter type supported hydrogenation catalysts, the reaction medium is contacted therewith by flowing the reaction medium over or through a bed of the catalyst, or by other contacting means known in the art.

The quantity of hydrogenation catalyst employed can vary over a broad weight range depending on the nature of the starting material and other processing conditions. For a batch type process, the quantity of hydrogenation catalyst normally can range between 1 and 30 weight percent, based on the weight of trialdehyde feed material, and preferably is in the range between about 1 and 10 weight percent.

The presence of water is required in the step (4) procedure to achieve the "hydrolysis-hydrogenation" reaction which theoretically is involved. The quantity of water employed is at least the stoichiometric amount required to interact hydrolytically with the trialdehyde feed material. Preferably, the quantity of water introduced into the reaction medium will vary between about one mole and 100 moles per mole of trialdehyde reactant, in a manner analogous to that described in U.S. Pat. No. 2,888,492.

Step (4) of the invention process preferably is conducted at a temperature in the range between about 180° C. and 225° C., and at a hydrogen pressure in the range between about 100 and 1000 psi.

For the high yield production of 1,4-butanediol, it is an essential requirement of step (4) that the pH of the reaction medium be maintained within the range between about 4 and 8, and preferably in the pH range between about 5 and 7.5. The conversion of straight chain trialdehyde and/or trihydric polyol can be accomplished essentially quantitatively if the pH of the reaction medium is maintained in a substantially neutral condition, i.e., a pH range between about 5 and 7.5. The yield of 1,4-butanediol product diminishes as the pH of the reaction medium increases in either acidity or basicity.

In accordance with another embodiment of step (4) of the present invention process, straight chain trialdehyde and/or trihydric polyol is contacted with hydrogen in the presence of a hydrogenation catalyst as described above in an aqueous medium having a pH between about 0.1 and 5.0 to yield tetrahydrofuran as the main product.

For the high yield production of tetrahydrofuran, it is an essential requirement of the step (4) procedure that the pH of the reaction medium be maintained within the range between about 0.1 and 5, preferably in the pH range between 0.2 and 3. The conversion of straight chain trialdehyde and/or trihydric polyol can be accomplished essentially quantitatively if the pH of the reaction medium is maintained in the preferred range, i.e., a pH range between about 0.2 and 3. The yield of tetrahydrofuran product diminishes as the pH of the reaction medium increases in basicity. If the pH of the reaction medium is in the range between about 5 and 7.5, then 1,4-butanediol is obtained as the main product instead of tetrahydrofuran. If the pH of the reaction medium is above 10, then the trialdehyde feed material undergoes diverse condensation-polymerization type reactions, and no tetrahydrofuran product is recoverable.

The pH of the reaction medium is conveniently maintained in the acidic range of pH by the addition of an appropriate quantity of a mineral acid such as sulfuric acid, or an organic acid such as acetic acid or p-toluenesulfonic acid. A polycarboxylic acid or an acidic ion-exchange resin may also be employed if desired. In the case of copper, nickel or iron catalysts, it is advantageous to employ a carboxylic acid as the acid component of the reaction mixture so as to maintain a high level of catalytic activity.

At the conclusion of the step (4) hydrolysis/hydrogenation procedure, the 1,4-butanediol or tetrahydrofuran product can be recovered directly from the reaction product mixture in any suitable manner. The hydrogenation catalyst, if dispersed as a fine powder, can be removed by filtration, centrifugation, or by other suitable means. For commercial scale operation, the process is preferably conducted in a continuous manner.

The present invention process is a convenient and efficient method for producing 1,4-butanediol on an economically feasible commercial scale.

The following Examples are further illustrative of the present invention. The reactants and other specific ingredients are presented as being typical, and various modifications can be devised in view of the foregoing disclosure within the scope of the invention.

EXAMPLE I

A catalyst was prepared by the rapid dropwise coaddition of 100 milliliters of a 1.0 molar AgNO₃, 0.49 molar Cd(NO₃)₂ solution and 100 milliliters of a 1.72 molar KOH solution to 400 milliliters of vigorously stirred doubly distilled water. About 19 grams of Cab-O-Sil H-5 silica (325 m²/g, Cabot Corp. Boston, Mass.)

were then thoroughly mixed with the resultant slurry of silver-cadmium coprecipitate. The slurry was filtered, and the filter cake was washed with about 600 milliliters of doubly distilled water. The filter cake was calcined in air at 250° C. for 16 hours. The resultant material was crushed and screened to yield a 50–80 mesh fraction. Bulk chemical analysis of this material indicated that it contained 54% $SiO_2$, 17.3% Cd, 27.5% Ag with 0.3% K also present. Powder X-ray diffraction studies revealed that the composition metallic silver crystallites and cadmium oxyhydroxide $Cd_3[O(OH)]_2$ of two types, and cadmium hydroxide $Cd(OH)_2$. The silica, being amorphous, contributed no significant X-ray diffraction pattern.

Approximately 2.62 grams of the prepared silver-cadmium catalyst was charged to a 0.925 cm i.d. by 28 cm reactor tube. Hydrogen gas at 200 psig was passed over the catalyst in the reactor tube at 500 SCCM and the temperature was increased from 21° C. to 175° C. over the course of one hour, at which time the gas was changed to one containing 1 part acrolein and 40 parts hydrogen. The reactor effluent was sampled using a gas sampling valve and gas chromatography. Table I summarizes the process conditions employed and the product yields obtained.

Powder X-ray diffraction examination of the used catalyst disclosed lines at 2.38, 2.06, 1.46 and 1.25 Å, which indicated that a silver-cadmium alloy of the α-type was present on the silica. Chemical analysis of the alloy determined the content as 61.4% Ag and 38.5% Cd by weight. No discrete Ag or Cd crystallites were detectable.

liters and the slurry was filtered. The filter cake was washed with 3000 milliliters of distilled water, calcined in air at 250° C. for 21.5 hours, and the resulting catalyst precursor was crushed and screened to yield a 50–80 mesh fraction. Chemical analysis indicated that the composition contained 49.6% $SiO_2$, 25.9% Ag, 18.6% Cd, and 0.4% K. Powder X-ray diffraction indicated that metallic silver and cadmium oxide, CdO, both of medium order were present at this stage, besides the amorphous $SiO_2$ which did not contribute detectable X-ray diffraction lines.

A 7.35 grams quantity of this catalyst precursor were placed in a 0.925 cm i.d. by 28 cm reactor tube. Under 499 psig hydrogen flowing at 1500 SCCM, the reactor was heated to 200° C. from 18° C., maintained at 200° C. for 15 minutes, and cooled to 125° C. over a total period of one hour. The hydrogen was then replaced by 1 part acrolein in 111 parts hydrogen. Table V summarizes the results based on the analysis of liquid products collected at −78° C. under reactor pressure.

A 2.71 gram quantity of the catalyst precursor was placed in a 0.55 cm i.d. by 28 cm reactor tube, and under 620 psig hydrogen flowing at 1500 SCCM the material was heated from 10° C. to 200° C. over a period of one hour. The catalyst was maintained at 200° C. for 15 minutes and then cooled rapidly to 125° C., at which time an acrolein/hydrogen stream replaced the pure hydrogen. Table V summarizes various reactor conditions and the composition of the liquid products collected in a trap held at −78° C. and reactor pressure.

X-ray diffraction analysis of the used catalyst indicated that the principal AgCd alloy was the α-phase.

TABLE I

| Mole Percent Acrolein In Feed | Catalyst Temp. °C. | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.2 | 125 | 206 | 7.2 | 2.9 | 73.8 | 26.2 | 0.0 |
| 2.3 | 175 | 198 | 6.9 | 41.4 | 76.2 | 22.0 | 1.8 |
| 0.9 | 175 | 500 | 17.6 | 97.4 | 76.8 | 11.2 | 12.0 |

EXAMPLE II

A solution of 34.1 grams $AgNO_3$ (0.20 mole) and 60.2 grams $Cd(NO_3)_2 \cdot 2H_2O$ (0.195 mole) in 200 milliliters of water was added simultaneously with a solution of 34.95 grams of 87.4% analytical reagent grade KOH (0.591 mole) in 200 milliliters of water to 400 milliliters of rapidly stirred distilled water. The pH of the supernatant phase after addition was 6.0. The volume of the suspension was increased to 1500 milliliters, and 1000 milliliters of Cab-O-Sil M-5 were added with vigorous stirring. The total volume was adjusted to 2000 milli- Bulk chemical analysis indicated that the average composition of the silver-cadmium alloy on silica was 58.2% Ag and 41.8% Cd.

TABLE II

| Mole Percent Acrolein In Feed | Catalyst Temp. °C. | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.90 | 125 | 502 | 18.7 | 61.0 | 72 | 15 | 11 |
| 0.89 | 150 | 504 | 18.8 | 82.0 | 76 | 14 | 8 |
| 0.89 | 175 | 501 | 18.7 | 99.4 | 66 | 3 | 31 |
| 0.90 | 180 | 502 | 18.7 | 99.7 | 68 | 1 | 31 |
| TABLE II-A | | | | | | | |
| 3.00 | 150 | 999 | 6.7 | 11.1 | 78.9[1] | 21.1 | 0.0 |
| 3.00 | 175 | 999 | 6.7 | 91.3 | 74.2[2] | 15.5 | 10.3 |

STY (Grams Allyl Alcohol/Liter Hour)
[1] 103
[2] 958

EXAMPLE III

A 28.77 gram quantity of analytical reagent grade KOH (0.446 mole) was added to 200 milliliters of distilled water, and the resultant solution was warmed to 100° C. With rapid stirring a solution of 25.26 grams $AgNO_3$ (0.149 mole) and 45.85 grams $Cd(NO_3)_2 \cdot 4H_2O$ (0.149 mole) in 100 milliliters of distilled water was added. The suspension was cooled and diluted by the addition of 1000 milliliters of 2° C. distilled water followed by 100 milliliters of Cab-O-Sil M-5. Additional distilled water was added to adjust the total volume to 1800 milliliters. The pH of the supernatant phase was 6.5.

The suspension was vacuum filtered, and the filter cake was washed with 2000 milliliters of distilled water and calcined in air at 250° C. for 20 hours. The catalyst precursor was then crushed and screened to provide a 50–80 mesh fraction. X-ray diffraction examination revealed principally CdO of medium order, and no detectable silver lines.

A 4.04 gram quantity of this material was placed in a 0.55 cm i.d. by 28 cm reactor tube. The reactor under 490 psig hydrogen flowing at 1500 SCCM was heated from 20° C. to 200° C., held at 200° C. for 15 minutes and cooled to 125° C. over the course of 1.6 hours. At this time, the hydrogen was replaced by 1 part acrolein in 109 parts hydrogen. Table VI summarizes various reactor conditions, and the resultant composition of liquid products collected in a trap held at −78° C. and reactor pressure. The used catalyst, 5.7% silica with 65.7% alloys, consisted of well ordered $\alpha,\gamma$ and some $\epsilon$-phase AgCd alloy on $SiO_2$. The average alloy composition was 52.4% Ag and 46.6% Cd.

position contained 18.8% $SiO_2$, 27.2% Ag and 30.6% Cd.

A 13.10 gram quantity of this material was placed in a 0.925 cm i.d. by 28 cm reactor tube. Under 100 psig gas (99% He, 1% $H_2$) flowing at 200 SCCM, the temperature was raised in 12 minutes to 75° C., then at 25° C. per hour to 250° C. and maintained at the final temperature for 65 hours. The catalyst was cooled to 125° C., and the gas stream was changed to 510 psig hydrogen flowing at 1500 SCCM. After 24 minutes, the gas was changed to 1 part acrolein in 113 parts hydrogen. Table VII summarizes various reactor conditions and the resultant composition of the liquid products collected in a trap held at −78° C. and reactor pressure.

The used catalyst had a nitrogen BET surface area of 9.6 m²/grams, and contained primarily $\gamma$AgCd, with $\alpha$ and some $\epsilon$ AgCd alloy, all on silica. The average composition of the AgCd alloys was 54.9% Ag and 45.1% Cd.

TABLE IV

| Mole Percent Acrolein In Feed | Catalyst Temp. °C. | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.87 | 125 | 515 | 20.0 | 19.1 | 77.0[1] | 12.5 | 1.6 |
| 0.87 | 150 | 515 | 20.0 | 69.7 | 79.7[2] | 10.0 | 4.1 |
| 0.88 | 175 | 510 | 19.9 | 99.2 | 68.5[3] | 0.8 | 27.3 |
| 0.87 | 160 | 515 | 20.0 | 85.5 | 78.0 | 8.0 | 14.0 |

STY (Grams Allyl Alcohol/Liter Hour)
[1] 13.3
[2] 47.0
[3] 84.9

EXAMPLE V

Two solutions were prepared by dissolving 34 grams $AgNO_3$ (0.20 mole), 30 grams $Cd(NO_3)_2 \cdot 4H_2O$ (0.097 mole) and 0.10 gram $Zn(CH_3COO)_2 \cdot 2H_2O$ (0.00046 mole) in 100 milliliters of doubly distilled water, and 25.4 grams of 87.4% analytical reagent grade KOH (0.396 mole) in 100 milliliters of distilled water. Both

TABLE III

| Mole Percent Acrolein In Feed | Catalyst Temp. °C. | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.91 | 125 | 494 | 7.9 | 3.9 | 69.2 | 18.0 | 4.4 |
| 0.89 | 150 | 503 | 8.1 | 10.8 | 77.7 | 19.3 | 1.0 |
| 0.89 | 175 | 506 | 8.1 | 55.0 | 78.7 | 12.8 | 9.8 |
| 0.89 | 190 | 506 | 8.1 | 97.6 | 70.9 | 5.1 | 23.1 |
| 0.91 | 200 | 496 | 7.9 | 99.1 | 61.2 | 2.7 | 35.7 |
| 0.89 | 182 | 506 | 8.1 | 86.0 | 77.5 | 11.0 | 11.5 |

EXAMPLE IV

To a solution of silver and cadmium nitrates containing 102 grams $AgNO_3$ (0.600 mole) and 138.9 $Cd(NO_3)_2 \cdot 2H_2O$ (0.450 mole) in 150 milliliters of distilled water, a solution of 60.9 grams of 98.6% analytical reagent grade NaOH in 150 milliliters of distilled water was added with rapid stirring. The resultant black gel turned light brown on suspending in an additional 1500 milliliters of doubly distilled water. The precipitate was separated from the solution by vacuum filtration, washed with 2000 milliliters and doubly distilled water, and then ground in a mortar and pestle with 150 milliliters of DuPont Ludox AS Colloidal Silica. The mixture was dried for 20 hours at 95° C., and calcined in air at 200° C. for 60 hours. The mixture was then crushed and screened to yield a 50–80 mesh fraction. The composolutions were rapidly and simultaneously added to 100 milliliters of vigorously stirred doubly distilled water. Then 400 milliliters of additional water were added to suspend the gelatinous precipitate, and 1000 milliliters of Cabot Cab-O-Sil M-5 and sufficient water to maintain fluidity and adjust the total volume to 1800 milliliters were added. After 2 hours of further stirring at room temperature, the suspension was allowed to settle 24 hours in the dark at 4° C. The supernatant, with a pH of 6.5, was then decanted and the precipitate removed from the rest of the solution by vacuum filtration. The filter cake, after washing with 2000 milliliters of distilled water, was calcined in air at 250° C. for 20 hours. The resulting solid was cooled to room temperature in a vacuum desiccator, and then crushed and sieved to yield a 50-80 mesh fraction. This composition analyzed as containing 53.7% $SiO_2$, 30.1% Ag, 14.5% Cd, 150 ppm Zn, and 0.4% K. Powder X-ray diffraction indicated that Ag, $Cd(OH)_2$ and 2 types of $Cd_2O(OH)_2$ crystallites exhibiting sharp diffraction lines were present.

About 6.5 grams of this material were placed in a 0.924 cm i.d. by 28 cm reactor tube. The tube was heated under 201 psig hydrogen flowing at 750 SCCM from 24° C. to 133° C. in the course of 30 minutes. At the end of the period, one part acrolein in 40 parts hydrogen replaced the pure hydrogen stream. Table I summarizes the reactor conditions and the resultant composition of the products collected in a trap held at −78° C. and reactor pressure just down stream from the catalyst bed.

On powder X-ray diffraction examination the used catalyst exhibited broad lines at 2.36, 2.04, 1.44, 1.23 Å with broad back reflection lines of medium intensity. These lines are ascribed to an α-phase silver-cadmium-zinc alloy with an average composition of 67.46% Ag, 32.51% Cd and 0.03% Zn on silica, although the form of the zinc is not definitely known.

cooled to room temperature, and crushed and sieved to yield a 50-80 mesh fraction. This material by bulk analytical techniques contained 51.3% $SiO_2$, 20.8% Ag, 13.3% Cd, 210 ppm Zn, and 0.6% K. Powder X-ray diffraction indicated that Ag, $Cd(OH)_2$, and CdO crystallites exhibiting sharp diffraction lines were present.

About 3.36 grams were placed in 0.55 cm i.d. by 28 cm reactor tube. The reactor was heated under 209 psig hydrogen flowing at 750 SCCM from 23° C. to 125° C. in 30 minutes. After an additional six minutes, 1 part acrolein in 40 parts hydrogen replaced the pure hydrogen.

Table II summarizes various reactor conditions and the resultant composition of the liquid products collected in a trap maintained at −78° C. and reactor pressure. The used catalyst, by powder X-ray diffraction, had broad lines ascribe to the α-phase AgCd alloy on silica. These alloys had an average composition of 60.959% Ag, 38.797% Cd, 0.062% Zn. These were no direct evidence as to the form of the zinc, although under the hydrogenation conditions it was probable that the zinc had been reduced and hence alloyed with the silver-cadmium.

TABLE V

| Mole Percent Acrolein In Feed | Catalyst Temp. °C. | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.20 | 125 | 203 | 15.2 | 52 | 70 | 21 | 6 |
| 2.20 | 150 | 203 | 15.2 | 91 | 69 | 21 | 10 |
| 2.20 | 175 | 204 | 15.2 | 98 | 63 | 9 | 27 |
| 0.96 | 115 | 498 | 19.9 | 52 | 75 | 21 | 3 |
| 0.88 | 125 | 510 | 20.4 | 55 | 76 | 21 | 2 |
| 0.89 | 135 | 508 | 20.3 | 64 | 76 | 21 | 3 |
| 0.89 | 150 | 504 | 20.2 | 97 | 69 | 21 | 10 |
| 0.89 | 160 | 504 | 20.2 | 99 | 69 | 3 | 30 |
| 0.89 | 142 | 405 | 20.3 | 88 | 76 | 21 | 3 |

TABLE VI

| Mole Percent Acrolein In Feed | Catalyst Temp. °C. | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.88 | 125 | 510 | 8.3 | 29.0 | 77 | 20 | 3 |
| 0.86 | 150 | 523 | 8.7 | 78.0 | 76 | 20 | 4 |
| 0.89 | 175 | 505 | 8.0 | 99.9 | 74 | 5 | 21 |
| 0.87 | 160 | 520 | 8.7 | 88.0 | 76 | 18 | 6 |

EXAMPLE VI

Two solutions were prepared by dissolving 34 grams $AgNO_3$ (0.20 mole), 30 grams $Cd(NO_3)_2.4H_2O$ (0.097 mole) and 0.50 gram $Zn(CH_3COO)_2.2H_2O$ (0.0023 mole) in 100 milliliters of distilled water, and 25.6 grams of 87.4% analytical reagent grade KOH (0.399 mole) were dissolved in 100 milliliters of distilled water. Both solutions were rapidly and simultaneously added to 100 milliliters of vigorously stirred distilled water. After 400 milliliters of additional water were added to suspend the gelatinous precipitate, 100 milliliters of Cab-O-Sil M-5 and sufficient water to maintain fluidity and bring the total volume to 1800 milliliters were added. After 2 hours of further stirring at room temperature, the suspension was allowed to settle 24 hours in the dark at 4° C. The supernatant, with a pH of 6.5, was then decanted and the precipitate removed from the rest of the solution by vacuum filtration. The filter cake, after washing with 2000 milliliters of distilled water, was calcined in air at 250° C. for 20 hours. The resulting solid was

EXAMPLE VII

Two solutions were prepared by dissolving 34.1 grams $AgNO_3$ (0.200 mole), 60.2 grams $Cd(NO_3)_2.4H_2O$ (0.195 mole) and 4.0 grams $Zn(NO_3)_2.6H_2O$ (0.0135 mole) in 100 milliliters of distilled water, and 39.70 grams 87.4% analytical reagent grade KOH (0.618 mole) in 100 milliliters of distilled water. The solutions were rapidly and simultaneously added to 200 milliliters of vigorously stirred distilled water. The volume was increased to 1000 milliliters with additional distilled water, and the suspension was stirred for 30 minutes. The pH of the supernatant phase was 6.5. About 500 milliliters of Cab-O-Sil M-5 were added along with sufficient water to maintain fluidity and to adjust the volume to 1800 milliliters. After 2 hours of stirring, vacuum filtration was used to form a filter cake which was washed with 2000 milliliters of distilled water. The material was calcined in air at 200° C. for 65 hours, cooled in a vacuum desiccator to room temperature, and crushed and sieved to yield at a 50-80 mesh fraction. The composition analyzed as containing 28.9% $SiO_2$, 36.7% Ag, 30.3% Cd, 1.2% Zn and 0.1% K. Powder X-ray diffraction examination indicated that CdO and some Ag crystallites were the principle species identifiable by medium-broad lines at 2.34, 2.04, 1.23 Å with a broad but very weak back reflection pattern.

A 3.08 grams quantity of catalyst was charged into a 0.55 cm i.d. by 28 cm reactor tube. Under 490 psig hydrogen flowing at 1400 SCCM the catalyst was heated over the course of 48 minutes from 19° C. to 125° C., at which point the hydrogen was changed to a stream of one part acrolein and 109 parts hydrogen. Table IV summarizes various reactor conditions and the resultant composition of the liquid products collected in a trap held at $-78°$ C. and reactor pressure.

The used catalyst on powder X-ray diffraction exhibited sharp lines at 2.41, 2.36, 2.09, 1.66, 1.48, 1.26 Å. It appeared that principally $\gamma$ and $\alpha$ with some $\epsilon$-phase AgCdZn alloy was present on the silica. Chemical analysis indicated that these alloys had an average composition of 53.66% Ag, 44.59% Cd, and 1.75% Zn.

TABLE VII

| Mole Percent Acrolein In Feed | Catalyst Temp. °C. | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.92 | 125 | 488 | 8.4 | 14.0 | 76 | 19 | 3 |
| 0.91 | 150 | 495 | 8.5 | 12.0 | 78 | 21 | 1 |
| 0.90 | 175 | 500 | 8.6 | 61.0 | 75 | 18 | 4 |
| 0.90 | 180 | 500 | 8.6 | 97.8 | 76 | 8 | 16 |
| 0.89 | 185 | 504 | 8.6 | 99.7 | 71 | 5 | 23 |
| 0.90 | 177 | 500 | 8.6 | 88.0 | 76 | 12 | 12 |

EXAMPLE VIII

This Example illustrates a method for the preparation of acrolein diallyl acetal.

Into a flask equipped with a condenser and a Dean-Stark water trap unit was charged 50 milliliters of stabilized acrolein, 102 milliliters of allyl alcohol, 450 milliliters of hexane and 0.0025 gram of p-toluenesulfonic acid.

Refluxing of the reaction mixture was commenced, and the progress of the reaction was determined by the quantity of water collected. Additional-p-toluenesulfonic acid was added, for a total of 0.0125 gram of acid catalyst.

After the reaction was completed, the acrolein diallyl acetal was recovered by vacuum distillation.

EXAMPLE IX

This Example illustrates the straight-chain selective hydroformylation of acrolein diallyl acetal to the corresponding trialdehyde derivative.

An autoclave equipped with a stirrer was charged with 10 grams of acrolein diallyl acetal, 77 grams of benzene, 30 grams of triphenylphosphine and 0.2 gram of rhodium carbonyl.

The autoclave was sealed and flushed with nitrogen. The autoclave was heated to 78° C., and then pressured with a constant 90 psi of 50/50 carbon monoxide/hydrogen from a flow regulated storage vessel.

After two hours, the autoclave was cooled and the contents were filtered. The benzene in the filtrate was removed under vacuum. The remaining filtrate liquid was cooled in an ice bath, and 100 milliliters of cold methanol were added to the cooled filtrate liquid. A solid precipitate of triphenylphosphine formed, and the precipitate was separated by filtration. The precipitate was washed with cold methanol.

The filtrate mother liquor was roto-evaporated to remove the methanol. A residual oil (10.5 grams) was determined by NMR to consist of the following components (excluding approximately 8% triphenylphosphine):

| Linear aldehyde | 75% |
| Branched aldehyde | 10% |
| Hydrogenated compounds | 8% |
| Olefinic compounds | 4% |

EXAMPLE X

This Example illustrates the hydrolysis/hydrogenation of the trialdehyde product of Example IX to 1,4-butanediol.

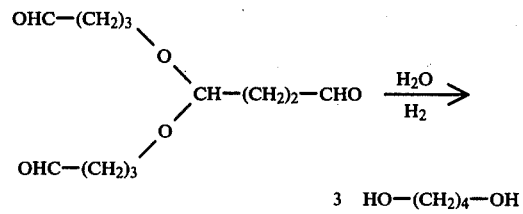

3 $HO-(CH_2)_4-OH$

An autoclave was charged with 10.14 grams of trialdehyde product of Example IX, 3 grams of Raney nickel and 30 grams of water.

The autoclave was sealed and flushed with hydrogen, and then pressured with about 1000 psi of hydrogen.

Stirring was commenced, and the autoclave was heated to a temperature of about 190° C. After three hours, the autoclave was cooled to room temperature and the contents were recovered. After filtering, the 1,4-butanediol product was identified by gas chromatographic analysis. The yield to diols was 77% of theoretical. The diol product ratio of 1,4-butanediol/2-methyl-1,3-propanediol was 88/12.

When the above described hydrolysis/hydrogenation process is conducted under acidic conditions (e.g., in the presence of 10 milliliters of acetic acid), the major product of the reaction is tetrahydrofuran.

What is claimed is:

1. A process for converting acrolein into 1,4-butanediol which comprises (1) selectively hydrogenating acrolein to a product mixture consisting of at least two moles of allyl alcohol per mole of acrolein and propionaldehyde, (2) subjecting the product mixture to acidic conditions to produce acrolein diallyl acetal and propionaldehyde diallyl acetal, (3) selectively hydroformylating the acetals to form a hydroformylation product mixture of

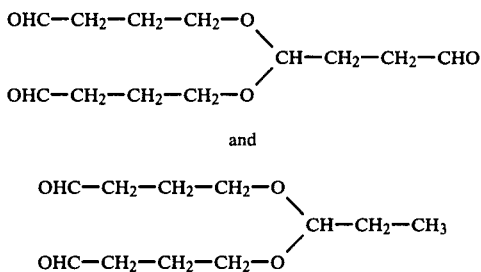

and and (4) subjecting the hydroformylation product mixture to substantially neutral aqueous hydrolysis/hydrogenation conditions to yield 1,4-butanediol.

2. A process in accordance with claim 1 wherein the selective hydrogenation of acrolein in step (1) is conducted in the presence of a silver-cadmium alloy catalyst, wherein the atomic ratio of silver to cadmium in the alloy is in the range of between about 0.1 and 3 to 1, and the silver-cadmium alloy exhibit an x-ray diffraction pattern which is substantially free of detectable unalloyed metal crystallite lines.

3. A process in accordance with claim 2 wherein the silver-cadmium alloy catalyst is supported on a carrier substrate.

4. A process in accordance with claim 1 wherein the selective hydrogenation of acrolein is conducted in the presence of a silver-cadmium-zinc alloy catalyst, wherein the atomic ratio of silver to cadmium in the alloy is in the range of between about 0.1 and 3 to 1, and the zinc is contained in the alloy in a quantity between about 0.001 and 30 weight percent, based on the total weight of alloy, and the silver-cadmium-zinc alloy exhibits an x-ray diffraction pattern which is substantially free of detectable unalloyed metal crystallite lines.

5. A process in accordance with claim 4 wherein the silver-cadmium-zinc alloy catalyst is supported on a carrier substrate.

6. A process in accordance with claim 1 wherein the acidic conditions in step (2) are provided by the presence of an acidic compound selected from strong inorganic and organic acids.

7. A process in accordance with claim 1 wherein the acidic conditions in step (2) are provided by the presence of a solid cation exchange resin in acid form.

8. A process in accordance with claim 1 wherein the selective hydroformylation step (3) is conducted in the presence of a catalyst complex of rhodium metal and phosphine ligand.

9. A process in accordance with claim 8 wherein the ratio of phosphine ligand to rhodium metal in the hydroformylation reaction medium is at least 400:1.

10. A process in accordance with claim 8 wherein the phosphine ligand is triarylphosphine.

11. A process in accordance with claim 10 wherein the triarylphosphine ligand is triphenylphosphine.

12. A process in accordance with claim 1 wherein the hydrolysis/hydrogenation step (4) is conducted in the presence of a hydrogenation catalyst.

13. A process in accordance with claim 12 wherein the hydrogenation catalyst is Raney nickel.

14. A process in accordance with claim 1 wherein the pH of the hydrolysis/hydrogenation reaction medium is between about 5 and 7.5.

* * * * *